United States Patent
Sargent

(10) Patent No.: US 8,632,762 B2
(45) Date of Patent: Jan. 21, 2014

(54) HAIR CONDITIONING COMPOSITION

(76) Inventor: Margaret J Sargent, Aiea, HI (US)

( * ) Notice: Subject to any disclaimer, the term of this patent is extended or adjusted under 35 U.S.C. 154(b) by 133 days.

(21) Appl. No.: 13/408,214

(22) Filed: Feb. 29, 2012

(65) Prior Publication Data

US 2013/0224143 A1 Aug. 29, 2013

(51) Int. Cl.
*A61K 8/97* (2006.01)
*A61K 8/92* (2006.01)
*A61Q 5/12* (2006.01)

(52) U.S. Cl.
USPC .......................................................... 424/74

(58) Field of Classification Search
None
See application file for complete search history.

(56) References Cited

U.S. PATENT DOCUMENTS

| | | | |
|---|---|---|---|
| 3,958,036 A * | 5/1976 | Latimer | 426/628 |
| 4,297,374 A * | 10/1981 | Wess | 514/777 |
| 6,544,534 B2 * | 4/2003 | Malmgren et al. | 424/401 |
| 6,723,309 B1 * | 4/2004 | Deane | 424/70.1 |
| 7,695,727 B2 * | 4/2010 | Magee et al. | 424/401 |
| 2004/0197364 A1 * | 10/2004 | Brown | 424/405 |
| 2005/0186171 A1 * | 8/2005 | Winick | 424/74 |
| 2007/0003632 A1 * | 1/2007 | Lapointe | 424/539 |
| 2009/0130220 A1 * | 5/2009 | Johnson | 424/539 |

* cited by examiner

*Primary Examiner* — Daniel Sullivan
*Assistant Examiner* — Peter Anthopolos

(57) ABSTRACT

The present invention is a hair conditioning composition includes approximately 40,000 IU of Vitamin E oil from 2 fl. oz., approximately 2 fl. oz. of 100% pure Australian tea tree oil, approximately 4 fl. oz. of Jojoba oil, approximately 32 oz. of pure extra virgin organic coconut oil with 62 percent MCT's and approximately 4 fl. oz. of 100 percent cold pressed sweet almond oil. The hair conditioning composition also includes approximately 4 fl. oz. of 100 percent pure Vitamin E, approximately 16 fl. oz. of cold pressed paraben free hexane free castor oil, approximately 16 fl. oz. of 100 percent moisturizing sweet almond oil and a plurality of avocados and whole aloe Vera plants weighing approximately 10 pounds of 100 percent pure fresh cut whole grown aloe Vera fresh plants.

4 Claims, No Drawings

HAIR CONDITIONING COMPOSITION

TECHNICAL FIELD & BACKGROUND

Many shampoos and conditioners on the market use harsh sulfates that can strip a person's hair of its natural oils. If an individual's hair doesn't have the necessary nutrients, it can become dry and brittle causing split ends and breakage.

The present invention generally relates to a hair related composition. More specifically, the invention is a hair conditioning composition.

It is an object of the invention to provide a hair conditioning composition that repairs and feeds damaged, dry or brittle hair and promotes hair growth.

It is an object of the invention to provide a hair conditioning composition that is made of all natural ingredients.

It is an object of the invention to provide a hair conditioning composition that enhances and improves the quality of a user's hair thickness and shine.

What is really needed is a hair conditioning composition that repairs and feeds damaged, dry or brittle hair and promotes hair growth that is made of all natural ingredients that enhances and improves the quality of a user's hair thickness and shine.

DETAILED DESCRIPTION OF ILLUSTRATIVE EMBODIMENTS

Various aspects of the illustrative embodiments will be described using terms commonly employed by those skilled in the art to convey the substance of their work to others skilled in the art. However, it will be apparent to those skilled in the art that the present invention may be practiced with only some of the described aspects. For purposes of explanation, specific numbers, materials and configurations are set forth in order to provide a thorough understanding of the illustrative embodiments. However, it will be apparent to one skilled in the art that the present invention may be practiced without the specific details. In other instances, well-known features are omitted or simplified in order not to obscure the illustrative embodiments.

Various operations will be described as multiple discrete operations, in turn, in a manner that is most helpful in understanding the present invention. However, the order of description should not be construed as to imply that these operations are necessarily order dependent. In particular, these operations need not be performed in the order of presentation.

The phrase "in one embodiment" is used repeatedly. The phrase generally does not refer to the same embodiment, however, it may. The terms "comprising", "having" and "including" are synonymous, unless the context dictates otherwise.

The composition of the present invention is a hair conditioning composition. More specifically, the hair conditioning composition is an aloe Vera and avocado based composition that consists of Vitamin E Oil, castor oil, jojoba oil, avocado, pure extra virgin coconut oil, aloe Vera, sweet almond oil and tea tree oil. The hair conditioning composition provides natural hair care for persons who use the hair conditioning composition with regular use. Many traditional shampoos and conditioners utilize harsh sulfates that can strip a person's hair of its natural oils. If an individual's hair doesn't have the necessary nutrients, it can become dry and brittle causing split ends and breakage. The hair conditioning composition promotes hair growth and consists of natural aloe, avocado, coconut and sweet almond oils and additionally adds body, bounce and shine. The hair conditioner also features vitamin E, jojoba, castor and tea tree oils. The hair conditioning composition is applied to a person's wet hair, which is then placed under a plastic shower cap and set under a steamer or dryer in the range of 10 to 20 minutes and is rinsed out of the person's hair and styled as usual. The hair conditioning composition may be readily available for purchase at retail stores where hair care products are sold. The hair conditioning composition features a plurality of rich nutrients to promote hair growth while adding relatively more body, bounce and shine to a person's hair. The hair conditioning composition is typically designed to be available in purple packaging with a photograph of aloe on the front of the packaging, which is typically in a bottle or other suitable package.

Example 1

The hair conditioning composition includes:

40,000 IU of Vitamin E oil from 2 fl. oz. from 1 bottle of Natures Gate 2 fl. oz. 100% pure Australian tea tree oil from the Vitamin Shoppe 4 fl. oz. of Jojoba oil from 1 jar from the Vitamin Shoppe 32 oz. from 2 jars of pure extra virgin organic coconut oil with 62 percent MCT's from Nature's Way 4 fl. oz. of 100 percent pure Hobe Naturals cold pressed sweet almond oil 4 fl. oz. 100 percent pure Vitamin E 16 fl. oz. from 1 bottle of cold pressed paraben free hexane free castor oil 16 fl. oz. from 1 bottle of Now Solutions 100 percent moisturizing sweet almond oil The castor oil has no preservatives, artificial color fragrance, mineral oil, paragons, or petroleum. The jojoba oil is derived from the natural plant extract with no yeast, wheat, corn, sugar, salt, soy, starch, dairy citrus, fish, animal derivatives, artificial colors or flavor added. The coconut oil efagold is certified organic, non GMO unrefined, non-bleached cold pressed, hexane-free and contains 62 percent MCTs-medium chain good fats. The sweet almond oil has relatively high levels of unsaturated triglycerides that moisturize a user's skin. Vitamin E has rich and pure antioxidant properties that include grape seed and safflower oil that provide a nourishing and moisturizing effect. The tea tree grown in Australia has no inherent antiseptic qualities. Four avocados and whole aloe Vera plants weighing approximately 10 pounds of 100 percent pure fresh cut whole grown aloe Vera fresh plants are also included in the hair conditioning composition.

While the present invention has been related in terms of the foregoing embodiments, those skilled in the art will recognize that the invention is not limited to the embodiments described. The present invention can be practiced with modification and alteration within the spirit and scope of the appended claims. Thus, the description is to be regarded as illustrative instead of restrictive on the present invention.

What is claimed is:

1. A hair conditioning composition comprising:
   whole avocado;
   whole aloe vera plant;
   jojoba oil;
   coconut oil;
   sweet almond oil;
   castor oil;
   tea tree oil; and
   Vitamin E.

2. The composition of claim 1, further comprising grape seed oil.

3. The composition of claim 1, further comprising safflower oil.

4. The composition of claim 1, wherein the whole aloe vera plant is fresh cut.

* * * * *